(12) United States Patent
Friend et al.

(10) Patent No.: US 8,937,197 B2
(45) Date of Patent: Jan. 20, 2015

(54) GOLD-CATALYZED SYNTHESIS OF CARBONATES AND CARBAMATES FROM CARBON MONOXIDE

(75) Inventors: Cynthia M. Friend, Lexington, MA (US); Robert J. Madix, Lexingon, MA (US); Bingjun Xu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/233,041

(22) PCT Filed: Jul. 16, 2012

(86) PCT No.: PCT/US2012/046944
§ 371 (c)(1),
(2), (4) Date: Mar. 21, 2014

(87) PCT Pub. No.: WO2013/012814
PCT Pub. Date: Jan. 24, 2013

(65) Prior Publication Data
US 2014/0221679 A1    Aug. 7, 2014

Related U.S. Application Data

(60) Provisional application No. 61/572,416, filed on Jul. 16, 2011.

(51) Int. Cl.
*C07C 269/04* (2006.01)
*C07C 68/00* (2006.01)

(52) U.S. Cl.
CPC ............. *C07C 269/04* (2013.01); *C07C 68/005* (2013.01)
USPC ........................................... 558/277; 560/157

(58) Field of Classification Search
None
See application file for complete search history.

(56) References Cited

U.S. PATENT DOCUMENTS 3,980,690 A * 9/1976 Cipriani et al. ............... 558/277

* cited by examiner

*Primary Examiner* — Michael Barker
*Assistant Examiner* — Po-Chih Chen
(74) *Attorney, Agent, or Firm* — Clark & Elbing LLP; Kristina Bieker-Brady

(57) ABSTRACT

The invention provides a method for producing organic carbonates via the reaction of alcohols and carbon monoxide with oxygen adsorbed on a metallic gold or gold alloy catalyst.

13 Claims, 9 Drawing Sheets

GOLD-CATALYZED SYNTHESIS OF CARBONATES AND CARBAMATES FROM CARBON MONOXIDE

CROSS-REFERENCE TO RELATED APPLICATIONS

This application is the national stage of international application no. PCT/US2012/046944, filed Jul. 16, 2012, which claims benefit of U.S. provisional application No. 61/572,416, filed Jul. 16, 2011, which is hereby incorporated by reference.

STATEMENT AS TO FEDERALLY SPONSORED RESEARCH

This invention was made with government support under DE-FG02-84-ER13289 awarded by the U.S. Department of Energy and under CHE-0952790 awarded by the National Science Foundation. The Government has certain rights in the invention.

FIELD OF THE INVENTION

The invention is in the fields of synthetic organic chemistry and catalysis, and relates specifically to a process for preparing carbonates and carbamates. More particularly, the present invention relates to a process for preparing carbonates and carbamates via oxidative carbonylation in the presence of a metallic gold catalyst.

BACKGROUND OF THE INVENTION

Dialkyl carbonates are industrially useful as lubricants, fuel additives, and reactive reagents in a wide variety of processes. In particular, dimethyl carbonate (DMC) has found use as an environmentally-acceptable solvent, high-octane oxygenated fuel additive, and esterifying and methylating agent, and the future demand for DMC is projected to exceed current global capacity. (Reviews: B. Schaeffner et al., Chem. Rev. 2010, 110:4554-4581; M. Pacheco and C. Marshall, Energy Fuels 1997, 11:2-29; P. Tundo and M. Selva, Acc. Chem. Res. 2002, 35:706-716.) DMC can also be used as a polymerizing agent in place of phosgene, enabling the production of polycarbonates and polyurethanes by melt transesterification.

Commercial success as bulk industrial solvents or fuels requires methods of synthesis of dialkyl carbonates that are scalable to multi-ton manufacturing, and that avoid costly or hazardous reagents, high pressures and temperatures, chemical wastes, and low-value by-products. In particular, methods that do not employ phosgene, chloroformates, or similarly corrosive and/or toxic intermediates are of considerable industrial value.

The industrial synthesis of dimethyl carbonate by reaction of methanol with phosgene has been largely displaced by a less hazardous and more environmentally benign process based on the catalytic oxidative carbonylation of methanol (Scheme 1):

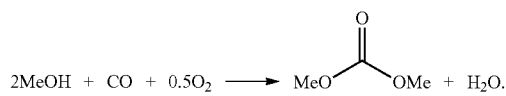

The carbonylation process is usually carried out using a copper(II) catalyst. The method was first reported by T. Saegusa et al., J. Org. Chem. 1970, 35, 2976-2978, refined by E. Perrotti and G. Cipriani (U.S. Pat. No. 3,846,468 (1974) and U.S. Pat. No. 3,980,690 (1976), and commercialized by Enichem in 1983. The so-called "Enichem Process" has been subject to an ongoing series of improvements and refinements ever since. (U. Romano et al., Ind. Eng. Chem. Prod. Res. Dev. 1980, 19:396-403; Z. Kricsfalussy et al., Ind. Eng. Chem. Res. 1998, 37:865-866.) Diethyl carbonate has been prepared by this means as well (B. Dunn et al., Energy Fuels 2002, 16:177-181; H. Xiong et al., Ind. Eng. Chem. Res. 2009, 48:10845-10849.) Cyclic carbonates have likewise been prepared from carbon monoxide and diols, using a palladium(II) catalyst (P. Giannoccaro et al., Organometallics 2006, 25:2872-2879.) W. Gaenzler et al., in U.S. Pat. No. 4,113,762 (1978), disclosed catalysts containing complexes of CuCl with chlorides of V, Cr, Fe, Co, Al, and Si. J. Hallgren, in U.S. Pat. No. 4,361,519 (1982), disclosed the use of redox catalysts based on Mn or Co, in combination with Ru, Rh, Pd, Os, Ir or Pt metals or complexes. The use of a gold/carbon anode in an electrochemical process for methoxylation of carbon monoxide has been reported (A. Funakawa et al., J. Phys. Chem. B 2005, 109:9140-9147.)

The direct synthesis of DMC from $CO_2$ and methanol is an attractive route, in theory, due to the low cost of $CO_2$ and the environmental desirability of processes that consume it, but the kinetic and thermodynamic stability of $CO_2$ are obstacles to efficient conversion that have yet to be overcome.

The copper-catalyzed reactions involve dissolved copper species such as Cu(OMe)Cl which tend to be poorly soluble in organic solvents. As a result, slow conversion rates and deactivation and leaching of copper(II) catalysts by co-product water are persistent problems, particularly in slurry processes, where the removal of water is difficult. Continuous-process variants have been developed, involving the energy-intensive volatilization, condensation, and isolation of product, and recycling of reactants (N. Di Muzio et al., U.S. Pat. No. 5,210,269 (1993)).

As is the case with most industrial-scale syntheses, a continuous oxidative carbonylation process employing heterogeneous catalysts would be much preferred, and continuous gas-phase processes using Co catalysts have been reported (D. Dreoni, D. Delledone et al., U.S. Pat. No. 5,322,958 (1994) and U.S. Pat. No. 5,457,213 (1995)). The existing gas phase processes for the oxidative carbonylation of alkanols are handicapped by low conversions, high pressures and/or high temperatures, and undesired by-products, as well as the hazards associated with potentially explosive oxygenated feed mixtures. There remains a need for efficient, cost-effective, heterogeneous catalytic syntheses of dialkyl carbonates.

For these and other reasons, there is ongoing research into alternative processes, catalysts and catalyst supports for DMC production. Several investigators, including the present inventors, have previously demonstrated that oxygen adsorbed onto gold and silver surfaces is activated toward the oxidation of a variety of substrates. (B. Xu, L. Zhou, R. J. Madix, C. M. Friend, Angew. Chem. Int. Ed. Engl. 2010, 49:394-398; X. Liu, R. J. Madix, C. M. Friend, Chem. Soc. Rev. 2008, 37:2243; I. E. Wachs, R. J. Madix, Surf. Sci. 1978, 76:531; D. M. Thornburg, R. J. Madix, Surf. Sci. 1990, 226: 61; J. L. Gong, T. Yan, C. B. Mullins, Chem. Commun. 2009, 761). The ability of gold to catalyze various oxidative reactions of carbon monoxide has been noted previously (M. A. Bollinger and M. A. Vannice, Appl. Catal. B: Env. 1996 8:417-443; W. Deng et al., Appl. Catal. A: Gen. 2005 291: 126-135; Q. Fu et al., Chem. Eng. J. 2003, 93:41-53; Y. Tai et al., *Appl. Catal. A: Gen.* 2004, 268:183-187; F. Bocuzzi et al., *J. Phys. Chem.* 1996, 100:3625-3631; F. Fajardie et al., PCT Intl. Appl. WO 2005/089937), and the carbonylation of methanol to form methyl formate has been carried out with gold catalysis (A. Wittstock et al., *Science* 2010 327:319.) It has not been previously known, however, that gold can serve as a catalyst for the oxidative carbonylation of alkanols with carbon monoxide and oxygen, to form dialkyl carbonates with high selectivity.

BRIEF DESCRIPTION OF THE INVENTION

It has now been discovered that metallic gold is a highly effective catalyst for the low-temperature oxidative carbonylation of alcohols without the use or production of toxic chemicals. The invention provides a method for the oxidative carbonylation of alcohols, mediated by contact with oxygen adsorbed on a metallic gold catalyst, as shown in Scheme 2.

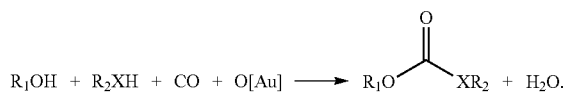

A specific embodiment, described herein in detail, is the synthesis of dimethyl carbonate ($R_1$=Me and $R_2$XH=MeOH), useful as an environmentally-friendly methoxycarbonylation and methylating reagent, solvent, fuel additive, polymer component, and transesterification reagent, by oxidative carbonylation of methanol. The metallic gold may optionally be modified by alloying with other metals and may be in bulk form, plated onto support surfaces, or dispersed in particulate form on refractory supports. The catalyst may be modified by incorporation of promoting agents such as inorganic salts, metal oxides, or metal oxide complexes. In the alcohol substrate $R_1$OH, $R_1$ may be C1-C8 straight chain alkyl, C3-C8 branched alkyl, C3-C8 cycloalkyl, or C6-C10 aryl. $R_2$XH may be an alcohol or secondary amine, i.e., X is O or $NR_2$. $R_2$ and $R_{2'}$ may be independently C1-C8 straight chain alkyl, C3-C8 branched alkyl, C3-C8 cycloalkyl, or C6-C10 aryl. When X is O, $R_1$ and $R_2$ may be the same or different. The process may take place at moderate temperatures (250-350 K) and does not require pressurization. Other features and advantages will be apparent from the following detailed description, the figures, and the claims.

DETAILED DESCRIPTION OF THE INVENTION

We have developed a direct, CO addition reaction facilitated by metallic gold for the synthesis of methoxycarbonyl, which has the potential for methoxycarbonylation of alcohols and amines (Ono, Y. Catal. Today 1997, 35, 15.), transesterification of glycerol to glycerol carbonate (Ochoa-Gomez, J. R.; Gomez-Jimenez-Aberasturi, O.; Maestro-Madurga, B.; Pesquera-Rodriguez, A.; Ramirez-Lopez, C.; Lorenzo-Ibarreta, L.; Torrecilla-Soria, J.; Villaran-Velasco, M. C. Appl. Catal., A 2009, 366, 315), as well as selective production of other related carbonate products, e.g., dialkyl carbonates and alkyl carbamates (Tundo, P.; Selva, M. Acc. Chem. Res. 2002, 35, 706). No halide promoter is necessary, and the reaction steps are distinct from those governing the classical carbonylation of methanol. There is precedence for formation of methoxycarbonyl by homogeneous Pd(II) phosphine complexes, identified using IR and NMR albeit at very high CO pressures (20-144 atm) (Rivetti, F.; Romano, U. J. Organomet. Chem. 1978, 154, 323). Even so, the products of these solution-phase reactions are dimethyl oxalate and acetic acid for both homogeneous Pd complexes and supported heterogeneous Pd (Gaffney, A. M.; Leonard, J. J.; Sofranko, J. A.; Sun, H. N. J. Catal. 1984, 90, 261).

Figure 1:
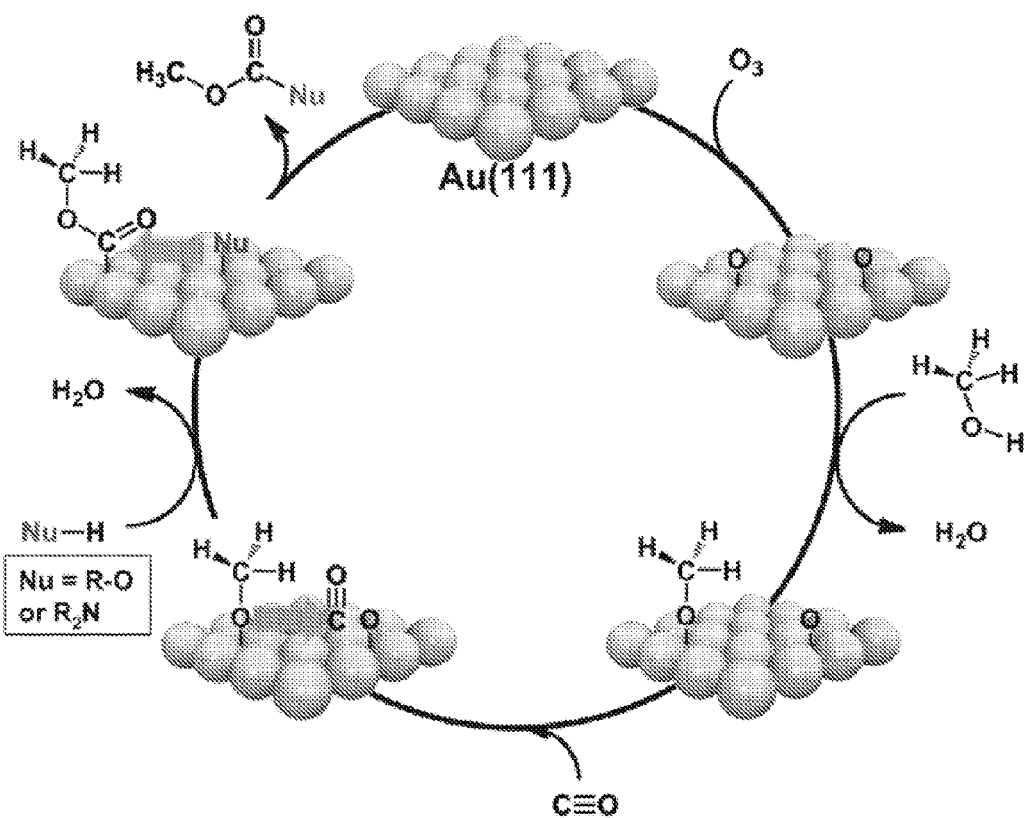
FIG. 1. Carbonylation of the surface-bound methoxy gives adsorbed methoxycarbonyl to which a surface nucleophile (Nu in the graphic, e.g., alkoxy or amide) adds to form the corresponding coupling product FIG. 2. (a) Temperature programmed reaction showing dimethyl carbonate ($CH_3O$—$C(=O)OCH_3$), methyl formate ($CH_3OC(H)=O$), $^{13}CO_2$, and water formed in the reaction of methanol with $^{13}CO$ on Au(111) activated by 0.1 monolayer (ML) of O. (b) The change in product selectivity for coupling products and $^{12}CO2$ (from combustion of methanol) on the amount of $^{—}CO$ dosed onto the methoxy-covered surface. (c) Pathways for the competing coupling pathways: oxidative self-coupling of methanol to methyl formate (upper) and coupling to CO yielding dimethyl carbonate (lower). The reactant dose used in part a corresponded to an integrated flux of 6 Langmuirs (L) (the equivalent of 6 layers) of methanol and 900 L of $^{13}CO$. Six L of methanol is used in all experiments in part b.

The basic principles governing the reactions of the methoxycarbonyl species on Au activated by oxygen are clearly illustrated and explained (FIG. 1). Primary emphasis is given here to the oxygen assisted catalytic carbonylation of methanol to synthesize dimethyl carbonate (FIG. 2, Nu=$CH_3O$, RO, or $R_2N$), a key "green" synthetic reagent, with mild reaction conditions without the production of toxic byproducts. The overall principle of the reactions is generalized by reactions with dimethylamine and other alcohols.

The potential impact of a green, heterogeneous process for methoxycarbonylation is broad. For example, dimethyl carbonate is used for major applications, including a fuel additive (Keller, N.; Rebmann, G.; Keller, V. J. Mol. Catal. A: Chem. 2010, 317, 1), a solvent (Miao, X. W.; Fischmeister, C.; Bruneau, C.; Dixneuf, P. H. Chem Sus Chem 2008, 1, 813), and a reagent in transesterification reactions critical to biodiesel production (Fabbri, D.; Bevoni, V.; Notari, M.; Rivetti, F. Fuel 2007, 86, 690); it is used for methylation and methoxycarbonylation processes in organic synthesis (Tundo, P.; Selva, M. Acc. Chem. Res. 2002, 35, 706). Moreover, large-scale production of dimethyl carbonate on an industrial scale is anticipated to increase in order to meet current and future demands: 170 tons/day were produced in 1997. China recently added a capacity of 267 000 ton/year (China Chemical Reporter; 2010), and the estimated future demand (300 000-600 000 ton/year) is 5-10 times that of the current U.S. production capacity (Pacheco, M. A.; Marshall, C. L. Energy Fuels 1997, 11, 2). Clearly, efficient catalytic production of dimethyl carbonate and/or an alternate route for methoxycarbonylation would have a major impact. Though it is a substitute for highly toxic reagents, such as methyl halides and phosgene ($COCl_2$), which were traditionally used as methylation reagents and produce halides as harmful byproducts (Tundo, P.; Selva, M. Acc. Chem. Res. 2002, 35, 706), its production is not without environmental impact, typically requiring high pressures and/or temperatures and yielding HCl as a byproduct (Keller, N.; Rebmann, G.; Keller, V. J. Mol. Catal. A: Chem. 2010, 317, 1).

Only oxygen, CO, and methanol are used in the direct carbonylation of methanol on gold. The potential advantages of the oxygen-assisted gold-catalyzed synthesis are that (1) it proceeds at low temperatures for a wide range of selective bond scission processes (Xu, B.; Zhou, L.; Madix, R. J.; Friend, C. M. Angew. Chem., Int. Ed. 2009, 49, 394; Xu, B.; Liu, X.; Haubrich, J.; Madix, R. J.; Friend, C. M. Angew. Chem., Int. Ed. 2009, 48, 4206; Xu, B.; Liu, X.; Haubrich, J.; Friend, C. M. Nat. Chem. 2009, 2, 61; Su, F. Z.; Liu, Y. M.; Wang, L. C.; Cao, Y.; He, H. Y.; Fan, K. N. Angew. Chem., Int. Ed. 2008, 47, 334; Klitgaard, S. K.; DeLa Riva, A.T.; Helveg, S.; Werchmeister, R. M.; Christensen, C. H. Catal. Lett. 2008, 126, 213; Lambert, R. M.; Williams, F. J.; Cropley, R. L.; Palermo, A. J. Mol. Catal. A: Chem. 2005, 228, 27; Hayashi, T.; Tanaka, K.; Haruta, M. J. Catal. 1998, 178, 566; Haruta, M.; Yamada, N.; Kobayashi, T.; Iijima, S. J. Catal. 1989,115, 301), (2) is tolerant to the presence of water, and (3) is potentially very selective. We show here that gold is, in fact, extremely active for production of dimethyl carbonate as well as other coupled organic carbonates when activated by atomic oxygen.

Metallic gold is the preferred pure metal catalyst. A suitable gold alloy is gold-silver, for example as described in U.S. Pat. No. 4,219,509, the contents of which are incorporated herein by reference in their entirety. The metallic gold or gold alloy may be used in bulk form, such as granules or a gauze, or it may be carried on an inert supporting material. A wide variety of supports for gold catalysts, and methods for depositing metallic gold thereon, are known in the art. (See for example Tsubota et al., *Preparation of Catalysts V*, 1991, Elsevier Science Publishers B. V., Amsterdam, p. 695; H. F. Rase, *Handbook of Commercial Catalysts: Heterogeneous Catalysts*, 2000, CRC Press, p. 283; G. C. Bond, C. Louis, and D. T. Thompson, *Catalysis by Gold*, Imperial College Press, London, 2006.)

Suitable supports include but are not limited to carbon, ceramics, and other refractory materials, such as alumina, silica, titania, ceria, and other metal oxides, metal hydroxides and salts, and combinations thereof. Supported gold catalysts are preferably in the form of fine particles, more preferably ultrafine particles on the order of 10-10,000 nm diameter. Methods for deposition of gold on the surface of oxide and hydroxide supports are described by Haruta et al. in U.S. Pat. Nos. 4,839,327 and 5,623,090, and by Clark et al. in U.S. Pat. No. 5,965,754, the contents of which are incorporated herein by reference for the teaching of methods of catalyst preparation. Vapor-phase deposition methods for preparation of ultrafine gold particles are described by L. Brey et al. in U.S. Pat. No. 7,727,931, the contents of which are incorporated herein in their entirety. Metallic supports in various forms (e.g., foils, foams, wools, and wires in various woven and non-woven forms), plated with gold or a gold alloy, may also be employed.

The catalyst may optionally be promoted by with additives and modifiers known in the art, including but not limited to metal halides, carbonates, sulfites, sulfates, nitrites, and nitrates; transition metal oxoanions, lanthanides, and alkali and alkaline earth metals. Examples of modified, supported gold catalysts are described in U.S. Pat. No. 7,727,931 and references therein.

The process of the invention may be conducted either in the gas or liquid phases. The reaction proceeds in the presence of oxygen adsorbed to the catalyst surface. The adsorbed oxygen may originate from a variety of known sources of unreduced or partially-reduced oxygen; suitable sources include but are not limited to added $O_2$, ozone (R. W. Joyner and M. W. Roberts, Chem. Phys. Lett., 1979, 60:459-462; B. K. Min et al., J. Phys. Chem. B. 2006, 110:19833), $NO_2$ (S. R. Bare et al., Surf. Sci., 1995, 342:185-198), and the like, or mixtures thereof. Molecular oxygen may also be derived from the ambient atmosphere.

The use of the method of the invention in continuous synthesis is exemplified by the following procedure: A rolled gold gauze is placed into a column, and a mixture of oxygen and an inert gas is fed through the column. The temperature may range from ca. 250 K to 350 K or more, and the pressure may range from 0.1 atm to several atmospheres. The pressure and concentration of oxygen are adjusted so as to produce between 0.1 and 0.2 L (monolayers) coverage of the exposed gold surface. Methanol is added to the gas stream and allowed to flow through the column, and when a steady state is achieved, carbon monoxide is introduced to the stream. The temperature, pressure, and partial pressures of oxygen, methanol, and carbon monoxide may be adjusted to optimize the yield and selectivity of the process. Produced dimethyl carbonate and water are recovered by condensation, and unreacted gases are returned to the system for recycling. Subsequent separation of dimethyl carbonate from entrained water, methanol, and methyl formate may be carried out by distillation, as disclosed for example in U.S. Pat. No. 5,214,185.

Figure 2:
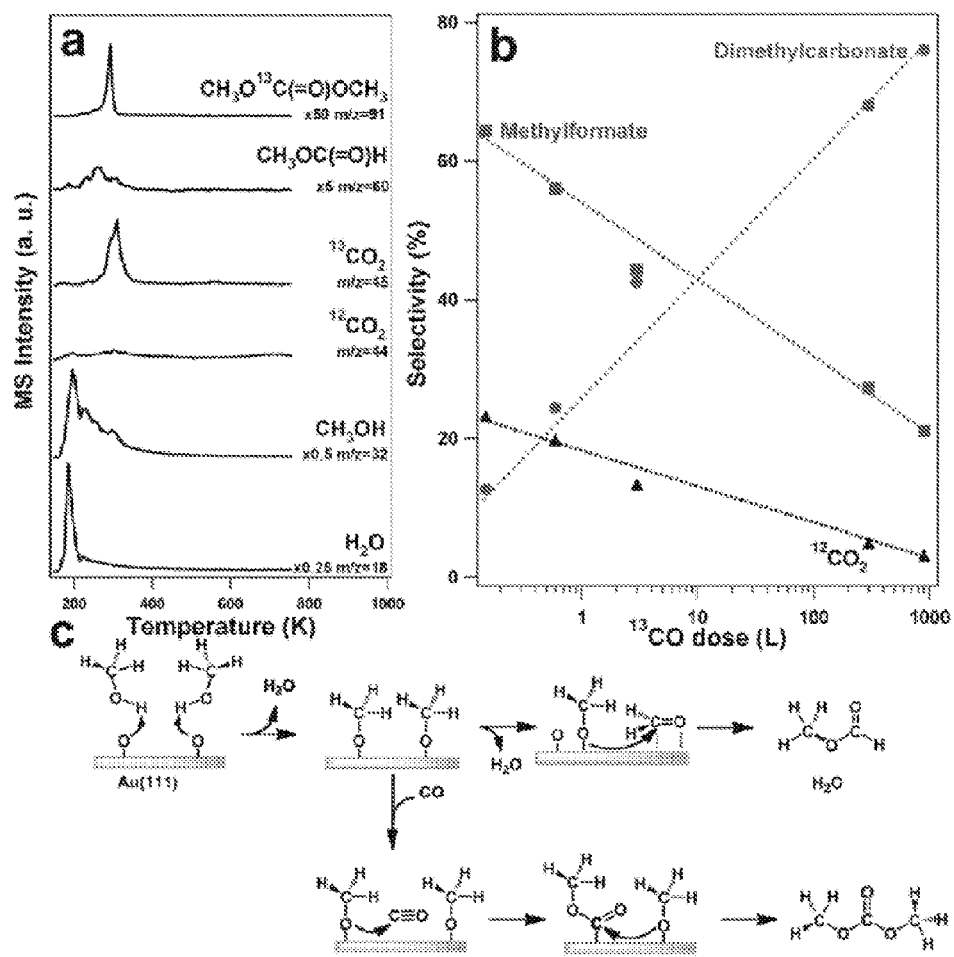

The direct carbonylation of methanol on metallic gold proceeds via nucleophilic attack on the carbon atom in CO by methoxy bound to the gold surface to yield the surface intermediate methoxycarbonyl (FIG. 1 and FIG. 2). In order to form dimethyl carbonate a second surface-bound methoxy then adds to this species. The methoxy is formed from selective activation of methanol by adsorbed atomic oxygen. The only byproducts of this reaction are water, $CO_2$, and methyl formate. In order to establish this mechanism methanol and $^{13}CO$ were sequentially introduced to a Au(111) surface with 0.1 monolayer of adsorbed atomic oxygen (O/Au(111)) at 150 K (FIG. 2). The oxygen was deposited using ozone decomposition under conditions that produce O-covered Au nanoparticles, most of which are ~2 nm in diameter (Min, B. K.; Alemozafar, A. R.; Pinnaduwage, D.; Deng, X.; Friend, C. M. J. Phys. Chem. B 2006, 110, 19833). Importantly, the oxygen is required for reaction. Methanol desorbs without reaction from either flat Au(111) or from Au(111) containing the Au nanoparticles from which the oxygen is first removed (Xu, B.; Friend, C. M.; Madix, R. J. Faraday Discuss. 2011, 152, 241). The carbonylation product, $CH_3O^{13}C(=O)OCH_3$, was produced upon heating (295 K) along with the self-coupling product, $CH_3OC(=O)H$ (methyl formate) (230 K). The activation energy of the carbonylation reaction is estimated to be ~75 kJ/mol, assuming a pre-exponential factor of $10^{13}$ s$^{-1}$. Unreacted methanol and secondary oxidation products also evolved from the surface (FIG. 2a).

Figure 8:
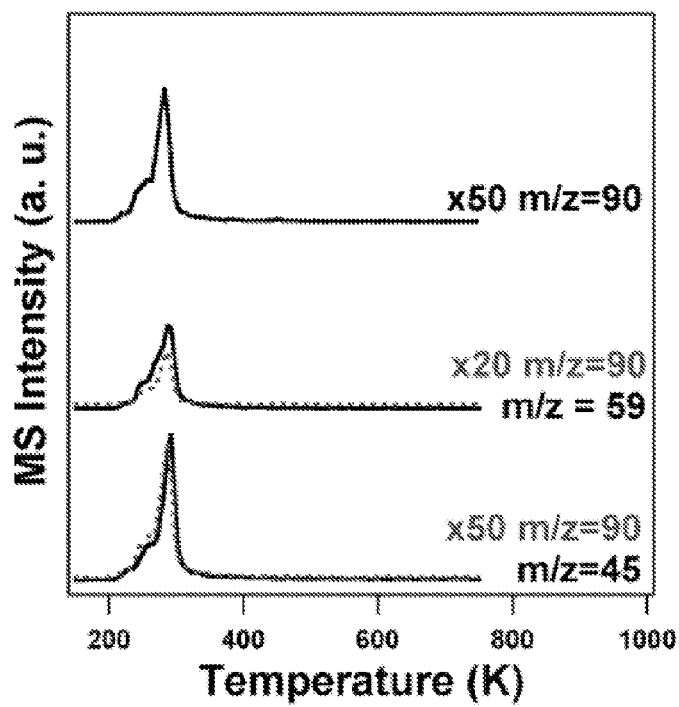
FIG. 8. Characteristic mass fragments (90, 59 and 45 amu, solid traces) of dimethyl carbonate produced in the methyl carbonylation reaction of methanol and CO on the O/Au(111) surface. Dashed traces are intensities of mass fragments 45 and 59 amu predicted using the mass intensity ratios (90 amu vs. 59 amu and 90 amu vs. 45 amu) obtained in a separate control experiment where neat dimethyl carbonate desorbs from Au(111) surface.

The use of $^{13}CO$ and $^{12}CH_3OH$ firmly establishes that two methoxy species react with a single $^{13}CO$. The only products other than $CH_3O^{13}C(=O)OCH_3$ that formed are unlabeled methyl formate, $^{13}CO_2$, $^{12}CO_2$, and $H_2O$. The small yield of $^{12}CO_2$ at the highest dose of $^{13}CO$ shows that the majority of combustion under the conditions of FIG. 2a is due to oxidation of $^{13}CO$, not methanol. Parallel studies of $^{12}CO$ with methanol on O/Au(111) verified that a single CO is incorporated into the product, on the basis of the mass shift of the product parent ion by one unit. Product identification was authenticated by quantitative comparison of the fragmentation patterns of the products and the corresponding neat samples or reference data from NIST (FIG. 8 and Table 1).

The competing pathway of oxidative self-coupling of methanol to methyl formate (FIG. 2c) was previously established from model studies on oxygen-covered Au(111) (Xu, B.; Liu, X.; Haubrich, J.; Madix, R. J.; Friend, C. M. Angew. Chem., Int. Ed. 2009, 48, 4206) and under catalytic conditions on nanoporous gold (Wittstock, A.; Zielasek, V.; Biener, J.; Friend, C. M.; Baumer, M. Science 2010, 327, 319). The salient features of the mechanism are that atomic O on Au initiates the reaction by inducing O—H bond scission to yield methoxy bound to the surface. Methyl formate is formed after a fraction of the methoxy eliminates a methyl hydrogen to produce formaldehyde. Attack of the electron-deficient carbon in formaldehyde by the remaining methoxy leads to the coupling product (Xu, B.; Liu, X.; Haubrich, J.; Friend, C. M. Nat. Chem. 2009, 2, 61). Importantly, elimination of hydrogen from adsorbed methoxy to produce formaldehyde is the rate-determining step for this reaction; thus, methoxy is sufficiently stable to be used as a reagent for the syntheses of the carbonate (FIG. 2c).

Figure 3:
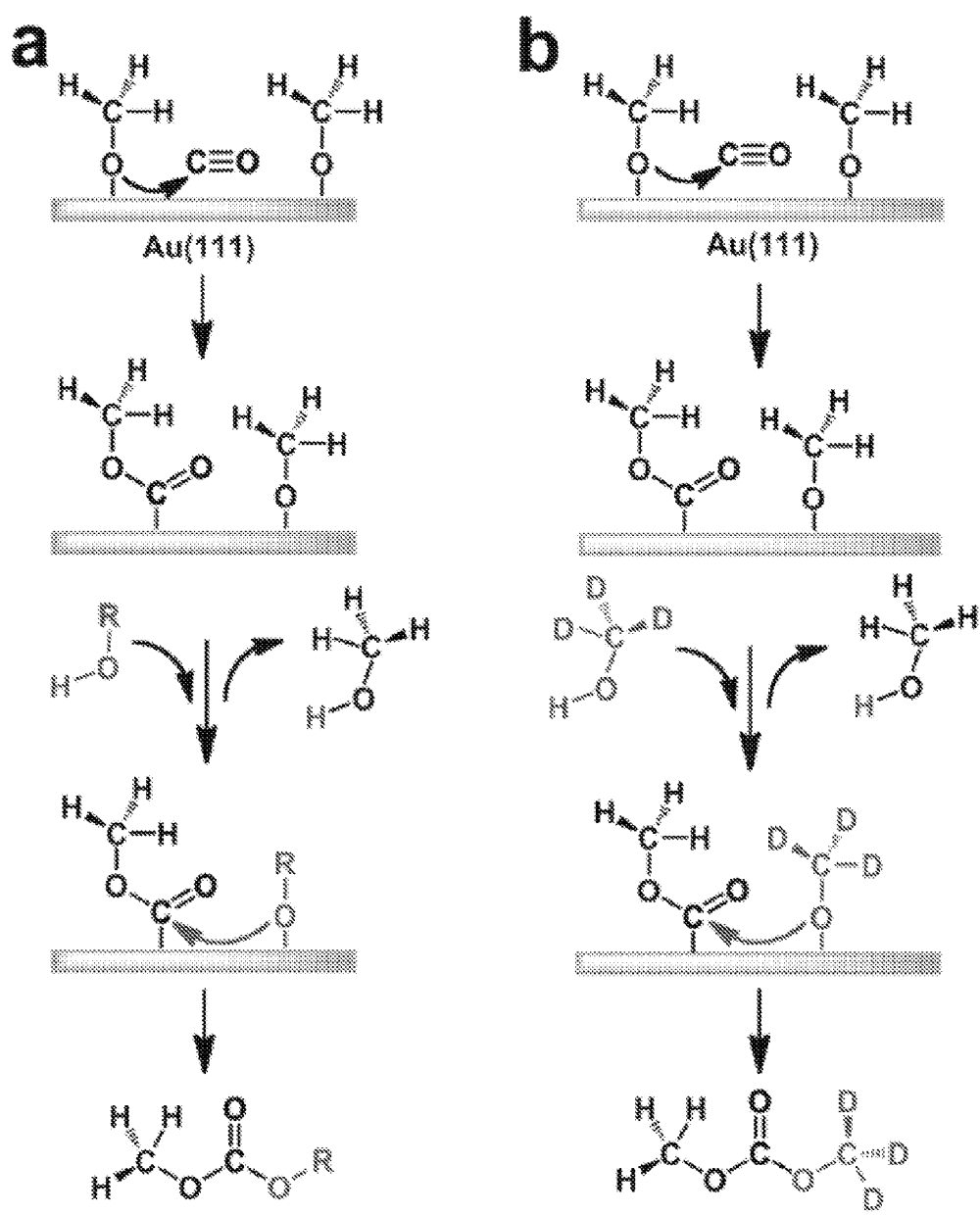
FIG. 3. (a) Schematic of the carbonylation process via two successive nucleophilic attacks to form "asymmetric" carbonylated product. (b) Schematic from part a exemplified by $CH_3O$(a) and $CD_3O$(a). The second nucleophile ($CD_3O$(a)) was introduced to the surface via the partial surface displacement between $CD_3OH$ and $CH_3O$(a).
Figure 9:
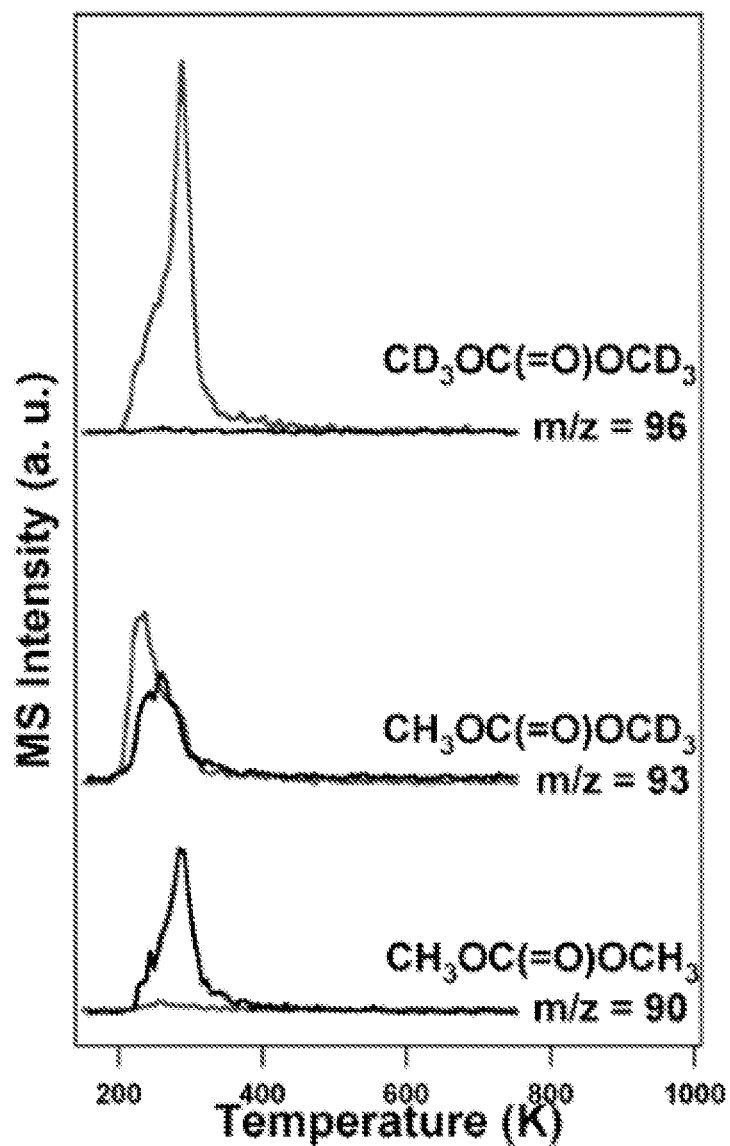
FIG. 9. The addition of $CD_3O$ after formation of $CH_3OC=O$ is illustrated using reactivity data. Only $CH_3OC(=O)OCH3$ (m/z 90) and $CH_3OC(=O)OCD_3$ (m/z 93) are detected (darker traces) when $CD_3OH$ is introduced to the surface after formation of $CH_3OC=O$ from reaction of methanol and CO on oxygen-covered Au(111) (0.1 monolayers of O). No $CD_3OC(=O)OCD_3$ was detected, clearly showing that no $CD_3OC=O$(a) is formed. Conversely, formation of $CD_3OC=O$ by reaction of $CD_3OH$ and CO first followed by introduction of CH3OH yields only $CH_3OC(=O)OCD_3$ and $CD_3OC(=O)OCD_3$ (lighter traces). These data illustrate are the supporting evidence for the scheme shown in FIG. 3.

The $CH_3OC=O(ads)$ intermediate is stable at 150 K, suggesting that the carbonylation to form dimethyl carbonate is a two-step process (FIG. 3a). The two-step nature of this methoxy addition was further verified by the introduction of $CD_3OH$ after formation of a coadsorbed mixture of $CH_3OCO$ and $CH_3O$, which adds adsorbed $CD_3O$ to the surface via an acid-base surface displacement of $CH_3O$ (FIGS. 3b and 9) (Xu, B.; Madix, R. J.; Friend, C. M. J. Am. Chem. Soc. 2010, 132, 16571). Subsequent heating initiates the nucleophilic attack of the methoxy carbonyl intermediate by $CD_3O(ads)$ to produce $CH_3OC—(=O)OCD_3$, clear evidence for the final reaction of the methoxy-(D) with adsorbed methoxycarbonyl. Spectroscopic data, described below, confirm the identification of the methoxycarbonyl ($CH_3OC=O$) intermediate and provide insight into its structure.

This two-step addition of nucleophiles to CO has potential utility for a broad range of important, large-scale synthetic processes. Methoxycarbonylation can be accomplished catalytically on oxygen-activated metallic gold, possibly obviating the need for dimethyl carbonate in alkylcarbonylation reactions, such as carboxymethylation and transesterification for which it is used (Ono, Y. Catal. Today 1997, 35, 15).

Figure 4:
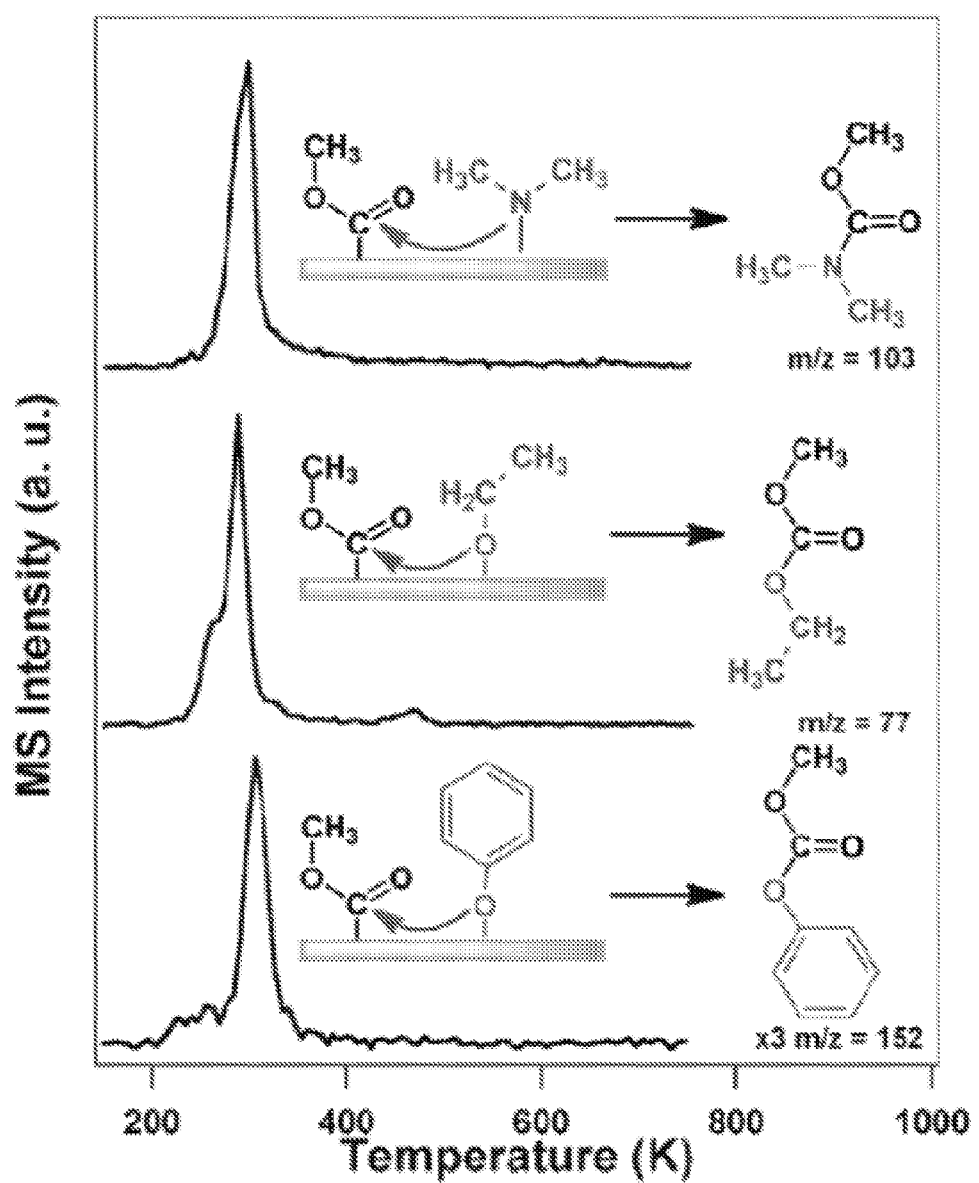
FIG. 4. Carboxymethylation via direct methoxycarbonyl transfer to dimethyl amide (top), ethoxy (middle), and phenoxy (bottom). The intermediates shown were created by reaction of dimethylamine, ethanol, and phenol with 0.1 ML adsorbed O. Parent ions of the products are shown in each case.
Figure 5:
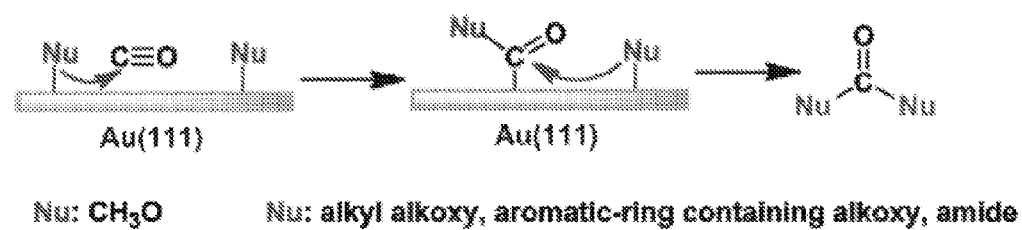
FIG. 5. Generalized two-step nucleophilic attack mechanism.

We have observed the formation of $CH_3OC(=O)OR$, where R is ethyl or phenyl, and production of $CH_3OC(=O)N—(CH_3)_2$ from reaction with dimethyl amine via direct methoxycarbonyl transfer to the adsorbed dimethyl amide and phenoxy on metallic gold (FIG. 4), demonstrating the generality of the reaction pathway reported here. Carbamates, formed by the surface-bound amide attacking the methoxycarbonyl intermediate, are widely used as herbicides, pesticides, drug intermediates, and precursors in the polymer industry (Gupte, S. P.; Shivarkar, A. B.; Chaudhari, R. V. Chem. Commun. 2001, 2620). The general two step nucleophilic attack mechanism is shown in FIG. 5, in which the first surface nucleophile attacks CO at low temperature (150 K) forming a stable surface-bound intermediate, which is then attacked by a second nucleophile at higher temperature (~300 K) forming the final product. Although different nucleophiles react with the methoxycarbonyl intermediate, we have not yet observed direct carbonylation of ethoxy, phenoxy, or dimethyl amide under the limited conditions tested. Nevertheless, the formation of methoxycarbonyl by CO addition to adsorbed methoxy provides a platform for a range of syntheses.

As expected from the mechanism shown in FIG. 1, the branching ratio for the two competing coupling pathways involving methanol and CO (methyl formate and dimethyl-carbonate production) depends strongly on the amount of $^{13}CO$ introduced to the surface covered by adsorbed methoxy (FIG. 2b). Exposure to a relatively small amount of $^{13}CO$ results in excess adsorbed methoxy, accounting for the dominance of methyl formate production and further combustion of methoxy by excess adsorbed oxygen (Xu, B.; Liu, X.;

Haubrich, J.; Madix, R. J.; Friend, C. M. Angew. Chem., Int. Ed. 2009, 48, 4206). Conversely, increasing the amount of $^{13}CO$ dosed increases the selectivity for dimethyl carbonate formation because a larger fraction of the adsorbed methoxy is converted to the adsorbed methoxycarbonyl, leading to more dimethyl carbonate. Ultimately, the selectivity can be increased to 75% dimethyl carbonate, with methylformate accounting for about 23% and a negligible amount of $^{12}CO_2$ (FIG. 2a). While the details have not been investigated for the other reactions of methoxycarbonyl with a second nucleophile, similar selectivity changes are expected (FIG. 2a).

The formation of the adsorbed methoxycarbonyl intermediate was confirmed using vibrational and photoelectron spectroscopies. The vibrational bands characteristic of methoxy are observed after introduction of methanol to the oxygen-covered surface at 150 K (Xu, B.; Liu, X.; Haubrich, J.; Madix, R. J.; Friend, C. M. Angew. Chem., Int. Ed. 2009, 48, 4206) (FIG. 6a, middle trace). After the surface-bound methoxy is exposed to CO, new vibrational peaks appear that signify formation of $CH_3OC=O(ads)$ (FIG. 6a, top trace). Comparison of the vibrational spectrum for dimethyl carbonate itself (FIG. 6a, bottom trace) with that of the intermediate (FIG. 6a, middle trace) shows that dimethyl carbonate is not yet formed under these conditions. There is precedence for formation of methoxycarbonyl in Pd(II)-phosphine complexes and on Ni(111) (Rivetti, F.; Romano, U. J. Organomet. Chem. 1978, 154, 323; Castonguay, M.; Roy, J. R.; Lavoie, S.; Adnot, A.; McBreen, P. H. J. Am. Chem. Soc. 2001, 123, 6429). (See Table 2, for vibrational assignments.)

Figure 7:
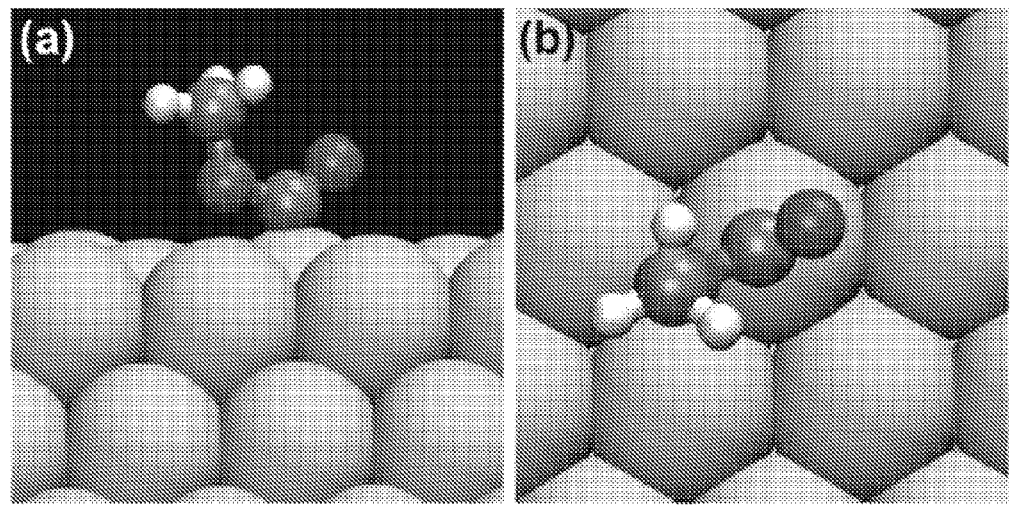
FIG. 7. Calculated structure of methoxycarbonyl on Au(111): (a) side view and (b) top view.

Density functional theory (DFT) calculations establish that methoxycarbonyl is a stable intermediate and provide the basis for vibrational assignments. On flat Au(111), the most favorable binding site of methoxycarbonyl is atop a single Au atom with the $CH_3$—O—C=O plane perpendicular to the surface (FIG. 7).

The band at 1655 cm$^{-1}$ is assigned primarily to the C=O double bond stretch on the basis of our calculations and analogous modes in organic esters (Table 2). The mode at 1040 cm$^{-1}$ is ascribed to the asymmetric $H_3C$—O—C stretch in the $CH_3OC=O(ads)$ (Table 2). Isotopic shifts further confirm these assignments. When $^{13}CO$ is used instead of $^{12}CO$, the v(C=O) mode shifts from 1650 to 1620 cm$^{-1}$, which agrees well with the predicted isotopic red shift of 29 cm$^{-1}$ (FIG. 6a, inset). Thus, the C atom of the C=O in the adsorbed methoxycarbonyl intermediate originates from CO (FIG. 3c). There is also a small (10 cm$^{-1}$) downward shift for the v(C—O) mode, which is consistent with the $^{13}C$ substitution. The weak band at 2065 cm$^{-1}$ is attributed to the C≡O stretch mode of a small amount of residual CO on the surface (Worz, A. S.; Heiz, U.; Cinquini, F.; Pacchioni, G. J. Phys. Chem. B 2005, 109, 18418). A more detailed analysis of experimental and computed vibrational frequencies is below, Table 3 and FIG. 10.

Since we know that gold nanoparticles form on our surface as a result of oxidation of Au(111),22 and since surface heterogeneities are present under most oxidative conditions (including catalytic conditions), DFT calculations were performed for a surface containing Au adatoms (1/9 monolayer) to evaluate whether defects alter the vibrational frequencies of this methoxycarbonyl species or its binding. The calculated vibrational frequencies shifted only slightly when methoxycarbonyl is adsorbed on an Au adatom, but the assignments remain the same. Binding of the $CH_3$—O—C=O to a Au adatom is more stable then on flat Au(111) by ~0.6 eV. To fully understand the role of defects, a thorough investigation of the activation energies for methoxycarbonyl formation on a variety of defects, including stepped surfaces, is required and is beyond the scope of this work.

Figure 11:
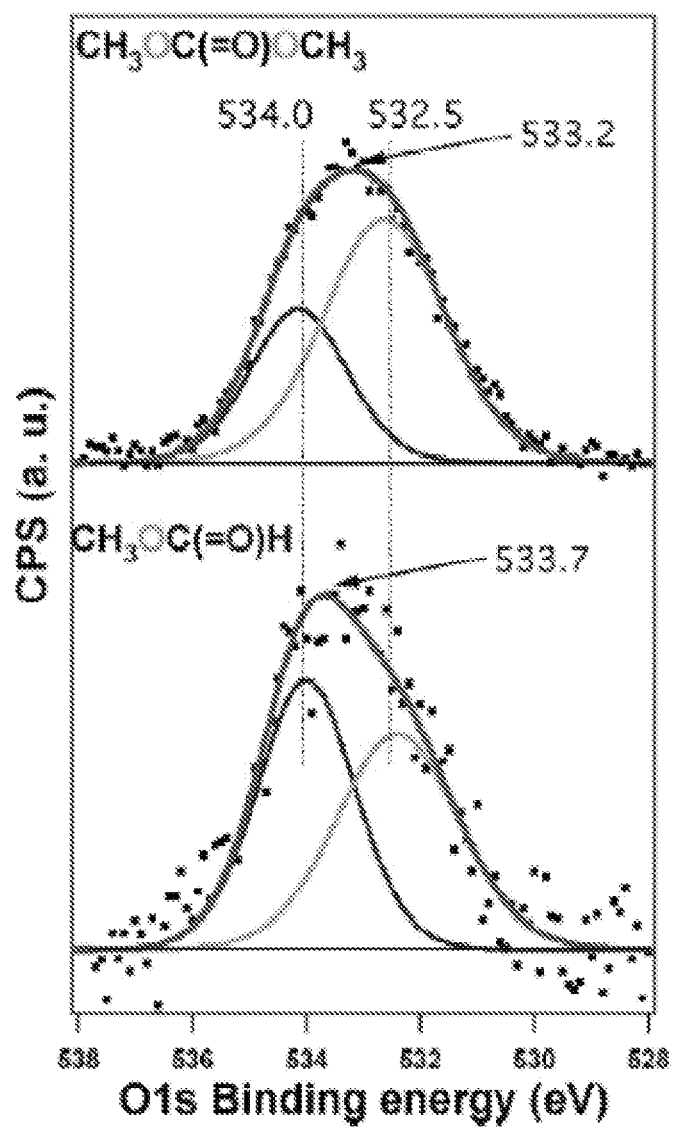
FIG. 11. X-ray photoelectron spectra of dimethyl carbonate (upper half) and methyl formate (lower half) adsorbed on Au(111) at 150 K. The envelopes (top curves) of the dimethyl carbonate and methyl formate spectra peak at 533.2 and 533.7 eV, respectively. The O1s peaks have contributions from oxygen in the methoxy (lower right curve) and carbonyl (lower left curve) group, with the binding energy of 532.5 and 534.0 eV, respectively. The ratio between the integrated peak area under lower left and right curves is 2:1 and 1:1 for dimethyl carbonate and methyl formate, respectively. The full widths at half max of the O1s peak for oxygen in the methoxy and carbonyl group are 2.5 and 2.0 eV, respectively.

Corresponding X-ray photoemission spectra provide further evidence for the $CH_3$—O—C=O intermediate and quantify the amount of conversion (FIG. 6b). Upon introduction of methanol at 150 K, an O(1s) peak characteristic of methoxy appears at 531.5 eV30 in addition to the peak for adsorbed atomic oxygen (529.4 eV) (Xu, B.; Zhou, L.; Madix, R. J.; Friend, C. M. Angew. Chem., Int. Ed. 2009, 49, 394; Min, B. K.; Alemozafar, A. R.; Pinnaduwage, D.; Deng, X.; Friend, C. M. J. Phys. Chem. B 2006, 110, 19833). Introduction of 300 L of CO at 150 K gives rise to peaks at 532.2 and 533.5 eV of equal magnitude (shown in blue in FIG. 6b-iii), consistent with the binding energies expected for adsorbed $CH_3$—O—C=O, based on model compounds (FIG. 11, Table 4).

The relevance of the invention to working catalytic processes is suggested by our previous studies of methanol esterification over nanoporous gold (Wittstock, A.; Zielasek, V.; Biener, J.; Friend, C. M.; Baumer, M. Science 2010, 327, 319). Model studies on metallic Au(111) activated by atomic oxygen show methanol esterification to methyl formate with nearly 100% selectivity. The selectivity and activity of this model catalyst directly parallel those of a nanoporous gold catalyst operated continuously at atmospheric pressure in flowing methanol and $O_2$. Similarly, there are strong parallels between our model studies of other coupling reactions on Au(111) and the product distributions of catalytic processes using either gold powder (Angelici, R. J. J. Organomet. Chem. 2008, 693, 847) or Au supported on metal oxides in solution (Klitgaard, S. K.; DeLa Riva, A. T.; Helveg, S.; Werchmeister, R. M.; Christensen, C. H. Catal. Lett. 2008, 126, 213; Wittstock, A.; Zielasek, V.; Biener, J.; Friend, C. M.; Baumer, M. Science 2010, 327, 319; Nielsen, I.; Taarning, E.; Egeblad, K.; Madsen, R.; Christensen, C. Catal. Lett. 2007, 116, 35). The ability to relate the chemical activity of gold under controlled conditions at lower pressures and lower temperatures to its behavior under higher pressure conditions is most likely due to the fact that gold itself is not very active for bond breaking processes; thus, the steady state coverage of oxygen and other reaction intermediates on Au is rather low, even at higher pressures, a condition that can be mimicked at lower pressure and temperature. Similar correspondence has been observed for the selective oxidation of methanol to formaldehyde on silver catalysts (Andreasen, A.; Lynggaard, H.; Stegelmann, C.; Stoltze, P. Surf. Sci. 2003, 544, 5; Wachs, I. E.; Madix, R. J. Surf. Sci. 1978, 76, 531). Hence, the invention provides the understanding of the mechanisms of these reactions as guidelines for designing catalytic processes.

The oxygen-assisted methoxycarbonylation pathway described in this work is fundamentally different from the classic carbonylation of methanol to acetic acid on Rh-based catalysts. In solution methanol is activated by HI, the resultant $CH_3I$ oxidatively adding to the Rh-complex. In our invention, methanol is activated by atomic oxygen adsorbed on the gold surface to form adsorbed methoxy and water, and no iodine-containing promoter is required.

CO inserts into the $CH_3O$—Au bond to form adsorbed methoxycarbonyl ($CH_3OCO$), whereas in the homogeneous process CO inserts into the $CH_3$—Rh bond to form acetyl. Lastly, in the gold-catalyzed methoxycarbonylation reported here a second nucleophile adds to the methoxycarbonyl to produce the products (e.g., carbonates, carbamates, FIG. 5), whereas reductive elimination of MeCOI with subsequent hydrolysis yields acetic acid in the Rh-catalyzed reaction. Though the mechanism of the carbonylation reaction on the supported gold catalyst is not yet known in detail, it appears strongly derivative of the homogeneous system. Iodide coordinated to Au is proposed to be an integral part of the active site for the carbonylation reaction (Goguet, A.; Hardacre, C.; Harvey, I.; Narasimharao, K.; Saih, Y.; Sa, J. J. Am. Chem. Soc. 2009, 131, 6973), and the products of the reaction are methyl acetate and acetic acid. Thus, the mechanism of carbonylation of the invention differs fundamentally from that of previously reported work.

Experimental Setup, Surface Cleaning, and Reactant Dosing. Experiments were performed in two separate ultrahigh vacuum (UHV) chambers. Temperature programmed reaction (TPR) and high resolution electron loss spectroscopy (HREELS) experiments were conducted in a UHV chamber with a base pressure below $2\times10^{-10}$ Torr. The single crystal Au(111) surface was cleaned by repeated Ar sputtering and annealing cycles, as confirmed by Auger electron spectroscopy (AES) and low energy electron diffraction (LEED) measurements (Min, B. K.; Alemozafar, A. R.; Pinnaduwage, D.; Deng, X.; Friend, C. M. J. Phys. Chem. B 2006, 110, 19833). The surface was first populated with 0.1 ML O (O/Au(111)) by dosing an appropriate amount of ozone at 200 K. The oxygen atom coverage was calibrated by comparing the amount of $O_2$ evolution at ~550 K in temperature programmed desorption to that evolved from a surface saturated with oxygen atoms, which is 1.1 ML (Saliba, N.; Parker, D. H.; Koel, B. E. Surf. Sci. 1998, 410, 270). The oxygen coverage reported is an average value, and the local oxygen coverage can deviate significantly from the mean value. The error in oxygen coverage on the Au(111) surface is ±15% due to day-to-day variation in $O_3$ concentration. Oxidation of the surface in this manner leads to release of Au atoms to form nanostructures containing Au and O, most of which are smaller than 2 nm in diameter (Min, B. K.; Alemozafar, A. R.; Pinnaduwage, D.; Deng, X.; Friend, C. M. J. Phys. Chem. B 2006, 110, 19833). Oxygen is primarily bound in local 3-fold coordination sites using this preparation.

Methanol and CO were sequentially introduced onto the oxygen covered surface at 150 K via leak valves. Exposures, corrected for dosing enhancement, are given here in terms of Langmuir (L, 1 Langmuir =$1\times10^{-6}$ Torr seconds). The total pressure rise in the vacuum chamber during the dosing of the reactants was used as a measure of the total exposure. Unless otherwise noted, 6 L was the typical dose.

Temperature Programmed Reaction Spectroscopy. Temperature programmed reaction experiments were used to determine product distributions and were performed according to well-established protocol (Min, B. K.; Alemozafar, A. R.; Pinnaduwage, D.; Deng, X.; Friend, C. M. J. Phys. Chem. B 2006, 110, 19833). In a typical experiment, Au(111) with reactants adsorbed was heated up linearly (~5 K/s) in front of a quadrupole mass spectrometer (Hiden HAL/3F). The selectivity for formation of different products is derived from experimental measurements analyzed using the following equation $$S_i = \frac{n_i}{\sum_i n_i}$$

in which $S_i$ is the selectivity toward product i and $n_i$ is the number density of the product i detected in the mass spectrometer. In the present case, the only products observed are dimethyl carbonate, methyl formate, $CO_2$, and water. No formaldehyde and formic acid were formed at a detectable level. The number density of product i is obtained using the integrated area under the signature mass peaks (90, 60, and 44 amu for dimethyl carbonate, methyl formate and $_{CO2}$, respectively), corrected for fragmentation, ionization cross-section, transmission coefficient, and detection efficiency (Xu, B.; Madix, R. J.; Friend, C. M. J. Am. Chem. Soc. 2010, 132, 16571.).

Vibrational and X-ray Photoelectron Spectroscopy. Vibrational spectra (FIG. 6a) were obtained using high resolution electron energy loss spectroscopy collected with an LK2000 spectrometer using a primary energy of 7.17 eV at 60° specular geometry. All spectra were taken at 150 K with a full width of half max 70-80 $cm^{-1}$. The X-ray photoelectron spectroscopy (XPS) experiments were conducted in a second chamber, with a base pressure below $5\times10^{-10}$ Torr. X-ray photoelectron spectra were acquired with an analyzer passing energy of 17.9 eV and a multiplier voltage of 3 kV using Mg Kα X-rays (300 W) as the excitation source. The binding energy (BE) calibration was referenced to the Au 4 $f_{7/2}$ peak at 83.9 eV. The O(1s) spectra were accumulated with 100 scans to enhance the signal-to-noise ratio.

The spectra in FIG. 6b were used to deconvolute the functional O(1s) binding energies due to different species on the surface. First, the peak position and width characteristic of atomic oxygen were obtained by using a single Gaussian peak to fit the trace in FIG. 6b-i. Subsequently, the spectrum in 6b-ii was used to obtain peak parameters for methoxy bound to gold by fitting with 2 Gaussian peaks, one of which uses the same parameters as for adsorbed oxygen (FIG. 6b-i); the other peak is attributed to methoxy. Finally, the trace in FIG. 6b-iii was fit with three Gaussians, two of which use the parameters for atomic oxygen and methoxy. The third peak was decomposed into two oxygen peaks, attributed to the inequivalent oxygens in methoxycarbonyl. These peaks were assigned by comparison to model compounds that contain the same functional groups, dimethyl carbonate and methyl formate (FIG. 11 and Table 4). The width and area of the peaks attributed to oxygen in the methoxy group and the carbonyl group of methoxycarbonyl were set to be identical in this final fitting process.

Product identification using mass spectrometry. Reaction products were identified by quantitative mass spectrometry using fragmentation patterns obtained from authentic samples; they were generally in good agreement with NIST reference data. The intensity ratio between masses 90, 59 and 45 amu produced in the methyl carbonylation reaction is very close to that of the control experiments, being 1:23:49, confirming the identification of the product (FIG. 8; Table 1). Methyl formate identification was performed as described previously(Xu, B.; Madix, R. J.; Friend, C. M. J. Am. Chem. Soc. 2010, 132, 16571).

TABLE 1

Relative Ion yields for the product of the reaction of $CH_3OH$ and CO on O/AU(111) compared to dimethyl carbonate

| Molecule | Ion | Product measured in temperature programmed reaction | Reference Data[a, b] |
|---|---|---|---|
| $(CH_3O)_2C=O$ | 90 (parent) | 1.00 | 1.00[a] |
|  | 59 | 0.23 | 0.20[a] |
|  | 45 | 0.49 | 0.50[a] |
| $CH_3OC(=O)N(CH_3)_2$ | 103 (parent) | 0.89 | 0.79[b] |
|  | 88 | 0.61 | 0.67[b] |
|  | 72 | 1.00 | 1.00[b] |
| $CH_3OC(=O)OC_2H_5$ | 77 | 0.49 | 0.40[b] |
|  | 45 | 1.00 | 1.00[b] |

TABLE 1-continued

Relative Ion yields for the product of the reaction of
CH₃OH and CO on O/AU(111) compared to dimethyl carbonate

| Molecule | Ion | Product measured in temperature programmed reaction | Reference Data[a, b] |
|---|---|---|---|
| $CH_3OC(=O)OC_6H_5$ | 152 (parent) | 0.85 | 1.00[b] |
| | 108 | 0.46 | 0.68[b] |
| | 78 | 1.00 | 0.71[b] |

[a]Calculated from temperature programmed desorption of authentic sample, corrected with transmission and detection coefficients
[b]Taken from NIST reference data Analysis of Vibrational spectra to establish the structure and identity of the methoxycarbonyl intermediate. Vibrational assignments for methoxy are based on previous studies in the literature. The peak at 1015 cm⁻¹ is the characteristic $v(H_3C-O)$.

TABLE 2

Vibrational assignments for methoxycarbonyl bound to Au(111).

| | Experimental (cm⁻¹) | | Calculated (cm⁻¹) | | | |
|---|---|---|---|---|---|---|
| | | | $CH_3OC=O$ | $CH_3O^{13}C=O$ | $CH_3OC=O$ | Gaseous[a, b] |
| Mode | $CH_3OC=O$ | $CH_3O^{13}C=O$ | flat surface | flat surface | on adatom | $CH_3OC(=O)CH_3$ |
| $v(C-H)_a$ | Not resolved | | 3117, 3082 | 3117, 082 | 3115, 3077 | 3031 |
| $v(C-H)_s$ | 2885 | | 2994 | 2994 | 2999 | 2964 |
| $v(C=O)$ | 1650 | 1620 | 1716 | 1676 | 1692 | 1771 |
| $\delta(C-H)_a$ | 1420[c] | 1425[c] | 1447, 1433 | 1447, 1433 | 1446, 1433 | 1430 |
| $\delta(C-H)_s$ | 1385 | 1391 | 1405 | 1404 | 1406 | 1375 |
| $\rho(C-H)$ | Not resolved | | 1154, 1116 | 1154, 1116 | 1156, 1117 | 980 |
| $v(C-O-C)_a$ | 1040 | 1030 | 1033 | 1015 | 1072 | 1248 |
| $v(C-O-C)_s$ | Not resolved | | 889 | 881 | 902 | 1060 |
| $\rho(CH_3-O-C=O)$ | 730 | 740 | 758 | 750 | 767 | 844 |

[a]from reference: T. Shimanouchi, Tables of Molecular Vibrational Frequencies Consolidated National Bureau of Standards, Washington, DC, 1972, Vol. 1. pp. 1-160.
[b]Normal mode assignments from P. Matzke et al. J. Mol. Structure 9 (1971) 255.
[c]Estimated by assuming symmetric peak shape for the $\delta(C-H)_s$ mode, but not resolved.

The vibrational assignments shown were made based on extensive isotopic substitution and by comparison with model compounds, such as methyl acetate (Table 3). The frequencies of the peaks characteristic of the methoxycarbonyl at 1040 and 1650 cm⁻¹ are similar to those reported for methoxycarbonyl bound to a Pd phosphine complex (1655 and 1070 cm⁻¹) (Rivetti, F.; Romano, U. J. *Organomet. Chem.* 1978, 154, 323). Notably, the frequency of the C—O—C asymmetric stretch of $CH_3OC=O$ on Ni was reported to be 1253 cm⁻¹ (Castonguay, M.; Roy, J. R.; Lavoie, S.; Adnot, A.; McBreen, P. H. *J. Am. Chem. Soc.* 2001, 123, 6429). The origin of this difference is not known, but may be due to differences in bonding on Au vs. Ni.

Figure 6:
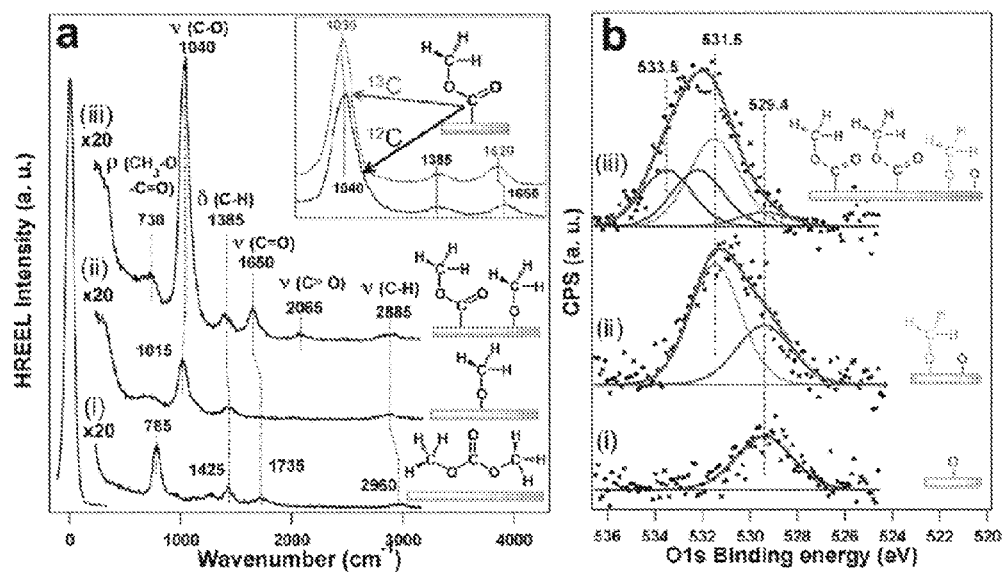
FIG. 6. Formation of the surface intermediate $CH_3OC=O$ (ads) is confirmed by both vibrational spectroscopy and X-ray photoelectron spectroscopy (XPS). (a) Electron energy loss spectra show the characteristic vibrations of (i) dimethylcarbonate, (ii) methoxy, and (iii) a mixture of methoxy and the surface intermediate, $CH_3OC=O$. The inset shows isotopic shifts in the spectra of $CH_3O^{12}C=O$ (ads) and $CH_3O^{13}C=O$(ads). (b) The evolution of surface species reflected by O(1s) binding energies measured using X-ray photoelectron spectroscopy: (i) 0.1 monolayer of oxygen on Au(111), (ii) after introduction of (i) to methanol (6 L or the equivalent of 6 layers) showing the formation of methoxy (O 1s BE=531.5 eV), and (iii) after introducing 300 L of CO to the surface to convert methoxy to the methoxy carbonyl intermediate peaks in blue at 533.5 and 532.2 eV are assigned to the C=O and $CH_3O$ moieties within methoxycarbonyl based on comparison with model compounds (FIG. 11 and Table 4). All experiments were performed at 150 K.

Density Functional Theory (DFT) Calculations and Vibrational analysis. All DFT calculations reported were performed using the VASP code (Kresse, G.; Hafner, *J. Phys. Rev. B* 1993, 47, 558; Kresse, G.; Hafner, *J. Phys. Rev. B* 1993, 48, 13115) with the GGA-PW91 functional (Perdew, J. P.; Wang, Y. *Phys. Rev. B* 1992, 45, 13244) to describe electron exchange and correlation. We employed the Projector Augmented Wave (PAW) function method (Kresse, G.; Joubert, D. *Phys. Rev. B* 1999, 59, 1758) with plane wave basis sets (cut-off: 400 eV). For reciprocal space, a 3×3×1 Monkhorst-Pack k-point grid was used. We tested a higher density F-centered 4×4×1 k-point in several cases and found no significant differences in either adsorption energies or in activation barriers (typical changes in these quantities were ~0.02 eV). The Au(111) surface was modeled by a 4-layer slab in the (111) direction, a p(3×3) unit cell in the lateral directions, and a vacuum of 15 Å between slabs; the 2 upper layers were allowed to relax, with the atoms in the bottom layer fixed at the ideal bulk positions. The bulk gold positions of the bottom layer were taken from the calculated lattice constant of 4.17 Å, which agrees well with the experimental value of 4.08 Å (Lide, D. R. *CRC Handbook of Chemistry and Physics*; CRC Press: New York, 1996). The electronic structure was converged to within $10^{-4}$ eV, and the geometries optimized until the forces were smaller in magnitude than 0.01 eV/A. Vibrational analysis of relaxed methoxycarbonyl structure was also carried out using the VASP code. Isotopically labeled methoxycarbonyl ($CH_3O^{13}C(=O)(a)$) was calculated by manually shifting the mass of the carbonyl carbon by 1 amu. Methoxycarbonyl was placed on the 3-fold, bridging (2-fold) and atop site of the Au(111) surface. The relaxed, lowest energy structure of methoxycarbonyl is for binding atop a gold atom via the carbonyl carbon atom (FIG. 6). The process of methoxy attacking CO forming methoxycarbonyl on Au(111) is exothermic by 1.23 eV, indicating that it is very favorable thermodynamically. The bond distances and angles are summarized in Table 3. The vibrational modes and the corresponding frequencies are summarized in Table 3.

Figure 10:
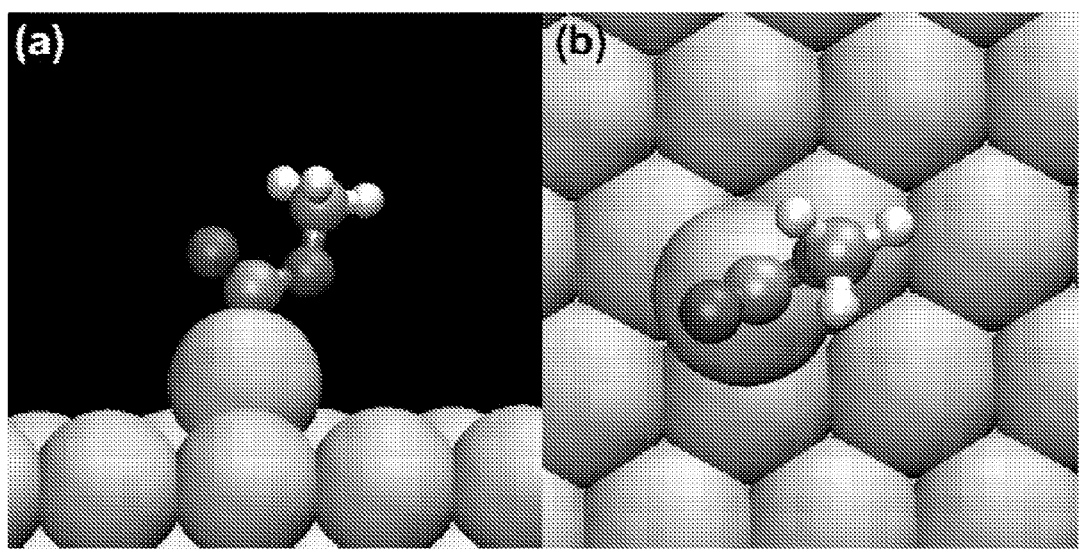
FIG. 10. Calculated structure of methoxycarbonyl adsorbed on a Au adatom on Au(111) surface: (a) side view and (b) top view.

The calculated isotopic shifts of the $v(C=O)$ (-40 cm⁻¹) and $v_a(C-O-C)_a$ (-18 cm-1) agree well with the measured shifts of —30 and —15 cm⁻¹. The calculated structure of methoxycarbonyl adsorbed on a Au adatom was also investigated to probe the effects of surface defects on Au(111) (FIG. 10). Methoxycarbonyl is more stable when adsorbed on a Au adatom than on a Au atom on Au(111) by 0.62 eV, which is calculated using the following formulae:

$$\Delta E_{ad} = E_1 - E_2 - E_{adatom}$$

$$E_{adatom} = E_{Au(111)+adatom} - E_{Au(111)}$$

in which $\Delta E_{ad}$, $E_1$, $E_2$, $E_{adatom}$, $E_{Au(111)+adatom}$, and $E_{Au(111)}$ are energy difference between methoxycarbonyl adsorbed on a Au adatom and on a Au atom on Au(111), total energy of the methoxycarbonyl and 1/9 ML adatom covered Au(111) system, total energy of the methoxycarbonyl and Au(111) system, energy of having a Au adatom on Au(111), total energy of the 1/9 ML adatom covered Au(111) and total energy of Au(111). $E_1$, $E_2$, $E_{adatom}$, $E_{Au(111)+adatom}$, and $E_{Au}(111)$ were calculated using DFT as described above.

TABLE 3

Bond distances and angles of the relaxed methoxycarbonyl structures.

| Bond | Distance (Å) | Bond | Angle (°) |
|---|---|---|---|
| Methoxycarbonyl adsorbed on flat Au(111) surface | | | |
| $H_2C$—H | 1.09 | H—C—H | 111.2 |
| $H_3C$—O | 1.46 | C—O—C | 115.3 |
| O—C=O | 1.35 | O=C—O | 124.9 |
| C=O | 1.21 | O—C—Au | 111.2 |
| C—Au | 2.10 | O=C—Au | 123.9 |
| Methoxycarbonyl adsorbed on a gold adatom on Au(111) surface | | | |
| $H_2C$—H | 1.10 | H—C—H | 111.2 |
| $H_3C$—O | 1.46 | C—O—C | 115.4 |
| O—C=O | 1.35 | O=C—O | 125.1 |
| C=O | 1.22 | O—C—Au | 110.6 |
| C—Au | 2.06 | O=C—Au | 124.3 |

X-ray Photoelectron Spectroscopy Studies

TABLE 4

X-ray photoelectron spectra O1s peak assignments

| Surface intermediate | Binding energy (eV) | Reference compound | Binding energy (eV) |
|---|---|---|---|
| $\mathbf{O}_{(a)}{}^a$ | 529.4 | $CH_3OC(=O)CH_3$ | 532.5 |
| $CH_3\mathbf{O}_{(a)}$ | 531.5 | $CH_3OC(=\mathbf{O})CH_3$ | 534.0 |
| $H_3COC=\mathbf{O}_{(a)}$ | 532.2 | $CH_3OC(=\mathbf{O})OCH_3$ | 532.5 |
| | 533.5 | $CH_3OC(=\mathbf{O})OCH_3$ | 534.0 |

$^a$O1s binding energies refer to the letters in bold:

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

The invention claimed is:

1. A method for preparing a carbonate or carbamate, by reacting $R_1OH$ with carbon monoxide and oxygen adsorbed on a metallic gold catalyst and $R_2XH$ according to the following scheme:

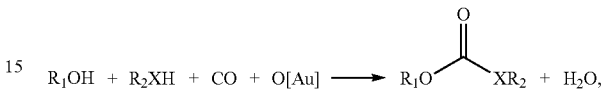

wherein X is O or $NR_{2'}$, wherein each of $R_1$, $R_2$, and $R_{2'}$ is independently selected from the group consisting of C1-C8 straight chain alkyl, C3-C8 branched alkyl, C3-C8 cycloalkyl, and C6-C10 aryl.

2. The method of claim 1, wherein X is O.

3. The method of claim 1, wherein X is $NR_{2'}$.

4. The method of claim 1, wherein the source of the adsorbed oxygen is $O_3$.

5. The method of claim 1, wherein the source of the adsorbed oxygen is $O_2$.

6. The method of claim 1, wherein $R_1$ is C1-C8 straight chain alkyl.

7. The method of claim 6, wherein $R_1$ is methyl.

8. The method of claim 1, wherein $R_2$ is C1-C8 straight chain alkyl.

9. The method of claim 8, wherein $R_2$ is methyl.

10. The method of claim 1, wherein X is O, and $R_1$ and $R_2$ are the same.

11. The method of claim 1, wherein X is O, and $R_1$ and $R_2$ are different.

12. The method of claim 1, wherein $R_{2'}$ is C1-C8 straight chain alkyl.

13. The method of claim 1, wherein $R_1OH$ is supplied in the gas phase, and the temperature is between 250 K and 300 K.

* * * * *